(12) United States Patent
Seo et al.

(10) Patent No.: US 6,903,177 B2
(45) Date of Patent: Jun. 7, 2005

(54) OLIGOMER FOR IMMOBILIZING PHYSIOLOGICAL MATERIAL, AND COMPOSITION FOR IMMOBILIZING PHYSIOLOGICAL MATERIAL COMPRISING THE SAME

(75) Inventors: Kang-Il Seo, Suwon (KR); Hun-Soo Kim, Seoul (KR); In-Ho Lee, Incheon (KR); Tai-Jun Park, Seoul (KR)

(73) Assignee: Samsung SDI Co., Ltd., Suwon (KR)

( * ) Notice: Subject to any disclaimer, the term of this patent is extended or adjusted under 35 U.S.C. 154(b) by 10 days.

(21) Appl. No.: 10/328,467

(22) Filed: Dec. 23, 2002

(65) Prior Publication Data

US 2003/0153069 A1 Aug. 14, 2003

(30) Foreign Application Priority Data

Jan. 14, 2002 (KR) .......................................... 2002-2052

(51) Int. Cl.[7] .............................................. C08G 77/26
(52) U.S. Cl. .............................. 528/38; 528/34; 528/37; 106/287; 106/11; 427/387; 428/447
(58) Field of Search .............................. 528/34, 38, 37; 106/287, 11; 427/387; 428/447

(56) References Cited

U.S. PATENT DOCUMENTS

| | | | | |
|---|---|---|---|---|
| 4,500,600 A | * | 2/1985 | Wong et al. | 428/391 |
| 5,858,653 A | | 1/1999 | Duran et al. | |
| 5,869,272 A | | 2/1999 | Bogart et al. | |
| 5,919,523 A | | 7/1999 | Sundberg et al. | |
| 5,981,734 A | | 11/1999 | Mirzabekov et al. | |
| 5,985,551 A | | 11/1999 | Brennan | |

\* cited by examiner

*Primary Examiner*—Kuo-Liang Peng
(74) *Attorney, Agent, or Firm*—Christie, Parker and Hale, LLP

(57) ABSTRACT

The present invention provides a silane oligomer for immobilizing a physiological material that is prepared by copolymerizing an aminosilane compound with a cyclic siloxane oligomeric compound. The present invention can preserve the immobilization layer by applying a silane oligomer. Further, the immobilization layer has a three-dimensional structure and thus has superior thermal stability and reagent resistance.

6 Claims, 3 Drawing Sheets

OLIGOMER FOR IMMOBILIZING PHYSIOLOGICAL MATERIAL, AND COMPOSITION FOR IMMOBILIZING PHYSIOLOGICAL MATERIAL COMPRISING THE SAME

CROSS-REFERENCE TO RELATED APPLICATION

This application claims priority of Korean Patent Application No. 2002-2052, filed Jan. 14, 2002, the entire disclosure of which is incorporated herein by reference.

FIELD OF THE INVENTION

The present invention relates to a silane oligomer for immobilizing a physiological material, a composition for immobilizing a physiological material comprising the same, and a biochip comprising the silane oligomer in an immobilization layer, and more particularly, to a silane oligomer for immobilizing a physiological material wherein the silane oligomer is environmentally friendly and has superior thermal stability and reagent resistance, a composition for immobilizing a physiological material comprising the silane oligomer, and a biochip comprising the silane oligomer in an immobilization layer with a uniform and high density immobilization functional group.

BACKGROUND OF THE INVENTION

Recently, demands for the development of technology used for analyzing the activity of physiological materials, such as nucleic acids, proteins, enzymes, antibodies, and antigens, have rapidly increased in the world. For such demands, a biochip in which the required physiological material molecules are immobilized on certain tiny regions by adopting semiconductor processing techniques is suggested, so thereby physiologically useful information is easily obtained just by biochemically searching the biochip.

The biochip is in the form of a conventional semiconductor chip, but what is integrated thereon is a bio-organic material such as an enzyme, a protein, an antibody, DNA, a microorganism, animal and/or plant cells and/or organs, a neuron, or the like. The biochip can be classified as a "DNA chip" immobilizing a DNA probe; a "protein chip" immobilizing a protein such as an enzyme, an antibody, an antigen or the like; or a "lab-on-a-chip" which is integrated with pre-treating, biochemical reacting, detecting, and data-analyzing functions to impart an auto-analysis function.

The biochip is a device used for diagnosing infectious diseases and analyzing genes by using an intrinsic function of physiological material and a mimicking function of a living body. It has recently become noteworthy as an essential device of a bio-computer which recognizes and responds to foreign stimulation like a living body and has a superior capacity to currently commercialized semiconductors.

To achieve the successful development of such a biochip, it is important to find a method for immobilizing a physiological material in which an interface between the physiological material and a substrate is efficiently formed, and the inherent functions of the physiological material can be utilized at a maximum level. Generally, the physiological material is immobilized on the surface of a glass plate, a silicon wafer, a microwell plate, a tube, a spherical bead, a surface with a porous layer, etc. by various techniques, for example, by reacting DNA with carbodiimide to activate a 5'-phosphate group of DNA and by reacting the activated DNA with a functional group on the surface of the substrate so as to immobilize the DNA on the substrate.

U.S. Pat. No. 5,858,653 discloses a composition comprising an ion group, such as a quaternary ammonium group, a protonated tertiary amine, or phosphonium, capable of reacting with a target physiological material; and a polymer having a photo-reactive group or a thermochemically reactive group for use in attaching to the surface of a substrate. U.S. Pat. No. 5,981,734 teaches that when DNA is immobilized by a polyacrylamide gel having an amino group or an aldehyde group, the DNA can be bound with a substrate via a stable hybridization bond to easily facilitate carrying out of analysis. U.S. Pat. No. 5,869,272 discloses an attachment layer comprising a chemical selected from dendrimers, star polymers, molecular self-assembling polymers, polymeric siloxanes, and film-forming latexes formed by spin-coating a silicone wafer with aminosilane. U.S. Pat. No. 5,869,272 discloses a method for the determination of a bacteria antigen by detecting a visual color change of an optically active surface. U.S. Pat. No. 5,919,523 discloses a method for preparing a support on which an amino silane-treated substrate is doped with glycine or serine or is coated with an amine, imine, or amide-based organic polymer.

In the above-mentioned patents, the immobilization layer is provided by preparing a self-assembly monolayer of silane molecules. Preferably, the silane is aminoalkoxy silane since it does not produce acidic by-products, and it can provide a molecular layer having a functional group with a relatively high density. Although much research has advanced the obtainment of a uniform monolayer having high-density functional groups using aminoalkoxy silanes, an aminosilane monolayer having a functional group with a uniform and high density and shorter manufacturing time has not been achieved.

U.S. Pat. No. 5,985,551 discloses a method for providing amino groups on a solid substrate by using a photolithography technique on the amino silane treated substrate, the method involving allotting hydrophilic functions on regions to immobilize DNA and fluorosiloxane hydrophobic functions on other regions so as to form a desirable patterned DNA spot on the substrate. This method is advantageous for controlling density of the functional groups by separating immobilizing regions from non-immobilizing regions. However, it has a problem in that the process is very complicated with multiple steps, so it has a longer manufacturing time and is thus inadequate for large-scale production.

SUMMARY OF THE INVENTION

The present invention provides a silane oligomer for immobilizing a physiological material which is prepared by copolymerizing an aminosilane compound with a cyclic siloxane oligomeric compound.

The present invention further provides a process for preparing the silane oligomer comprising: mixing the aminosilane compound with the cyclic siloxane oligomeric compound; adding water to the mixture to prepare an aqueous solution; and copolymerizing the aminosilane compound with the cyclic siloxane oligomeric compound while agitating the aqueous solution to obtain the silane oligomer in hydrate.

The present invention still further provides a composition for forming an immobilization layer for immobilizing a physiological material comprising a silane oligomer which is prepared by copolymerizing an aminosilane compound with a cyclic siloxane oligomeric compound.

The present invention also provides a method for fabricating a substrate for immobilizing a physiological material comprising coating the composition comprising the silane oligomer on the substrate, and heat-treating the coated substrate to prepare a three-dimensional cross-linking structural immobilization layer through condensation of the silane oligomer.

The present invention also provides a biochip comprising a physiological material immobilized on the surface of the immobilization layer of the substrate.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, wherein.

DETAILED DESCRIPTION OF THE PREFERRED EMBODIMENTS

Figure 1:
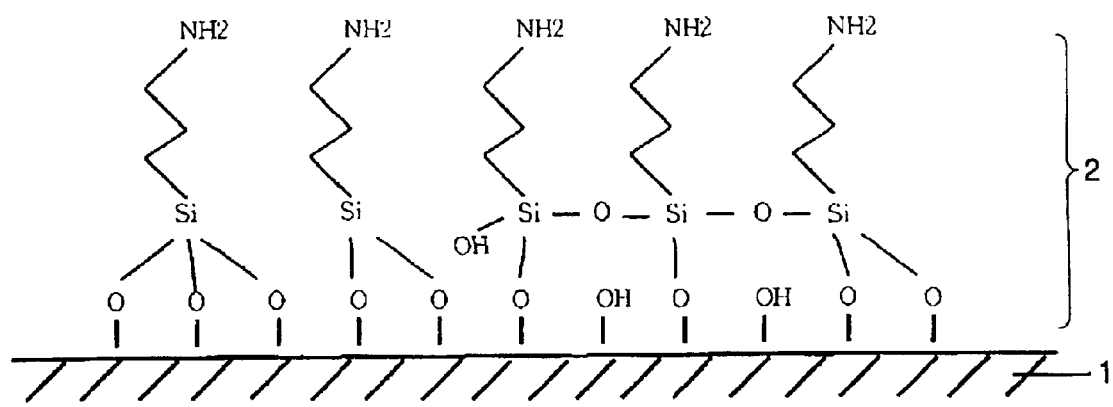
FIG. 1 is a cross-sectional view showing a conventional self-assembly-monolayer.

Hereinafter, the present invention is described in further detail.

The term "physiological material" herein means one derived from an organism or its equivalent, or one prepared in vitro. It includes, for example, enzymes, proteins, antibodies, microbes, animal and plant cells and organs, neurons, DNA and RNA, and preferably DNA, RNA, and proteins, wherein the DNA may include cDNA, genome DNA, and oligonucleotides; the RNA may include genome RNA, mRNA, and oligonucleotides; and the protein may include antibodies, antigens, enzymes, peptides, etc.

The term "biochip" herein means a semiconductor-like device that is prepared by combining a physiological material with an inorganic substrate.

Herein, the term "immobilization layer" means the coating layer of any compound having immobilization functional groups used in immobilizing the physiological material.

The silane oligomer of the present invention is used for preparing the immobilization layer, wherein the silane oligomer is prepared by copolymerizing an aminosilane compound represented by the following formula (1) with a cyclic siloxane oligomeric compound represented by the following formula (2):

(1)

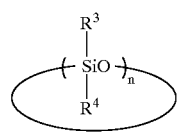
(2)

wherein $R^1$ is selected from the group consisting of hydroxy, and $C_{1-14}$ alkoxy, and is preferably hydroxy, methoxy, ethoxy, or acethoxy;

$R^2$ is selected from the group consisting of $C_{1-4}$ alkyl groups, $C_{6-20}$ aromatic groups, ether groups, ester groups, and imine groups, and is preferably a methyl group, an ethyl group, a propyl group, or a butyl group;

$R^3$ is a $C_{1-12}$ alkyl, preferably a methyl group, an ethyl group, a propyl group, and more preferably a methyl group;

$R^4$ is selected from the group consisting of hydroxy, $C_{1-14}$ alkoxy, halogen and combinations thereof, and is preferably hydroxy, methoxy, ethoxy, or acethoxy; and n is an integer ranging from 5 to 30.

When either the carbon number of $R_3$ (alkyl) is more than 12 or n is more than 30, the viscosity of the coating composition comprising the silane oligomer increases, which is disadvantageous for the coating process.

Preferred examples of the compound of formula (1) include 3-aminopropyltrimethoxysilane, 3-aminopropyltriethoxysilane, 2-aminoundecyltrimethoxysilane, aminophenyltrimethoxysilane, and N-(2-aminoethylaminopropyl)trimethoxysilane, but they are not limited thereto.

The compound of formula (2) can control the hydrophilicity of the immobilization group and improve the thermal stability of the three-dimensional cross-linking structure of the immobilization layer. The compound of formula (2) is exemplified by a methylsiloxane oligomeric compound, preferably a cyclic siloxane oligomeric compound where n of the formula (2) is 9 to 10, but it is not limited thereto.

The silane oligomer is prepared by a process comprising: mixing the aminosilane compound of the above formula (1) with the cyclic siloxane oligomeric compound of the above formula (2); adding water to the mixture to prepare an aqueous solution; and copolymerizing the aminosilane compound of formula (1) with the cyclic siloxane oligomeric compound of formula (2) while agitating the aqueous solution to obtain the silane oligomer in hydrate.

The silane oligomer hydrate is produced in an aqueous solution, and therefore it is relatively easier to synthesize compared to when water is not used.

In order to increase the copolymerization reaction rate, any organic or inorganic acid, such as acetic acid, nitric acid, hydrochloric acid, or the like, is added so that the pH of the aqueous solution is adjusted to from 4 to 10 before the copolymerization reaction.

The aminosilane compound of formula (1) and the cyclic siloxane oligomeric compound of formula (2) are preferably used in a mixed ratio of 0.01:99.99 to 90:10. If the amount of the aminosilane compound is less than 0.01, the amino group for immobilizing the physiological material is deficient. Whereas, if the amount of the aminosilane compound is more than 90, it is difficult to control the hydrophilicity of the immobilization group and thus the adding effect of the compound of formula (2) is not effective.

The copolymerization reaction during agitating is preferably performed at a temperature of 0 to 100° C. for 1 to 14 hours.

The copolymerization reaction is conducted in solution to produce the silane oligomer hydrate. An example of the silane oligomer hydrate is represented the following formula (3):

(3)

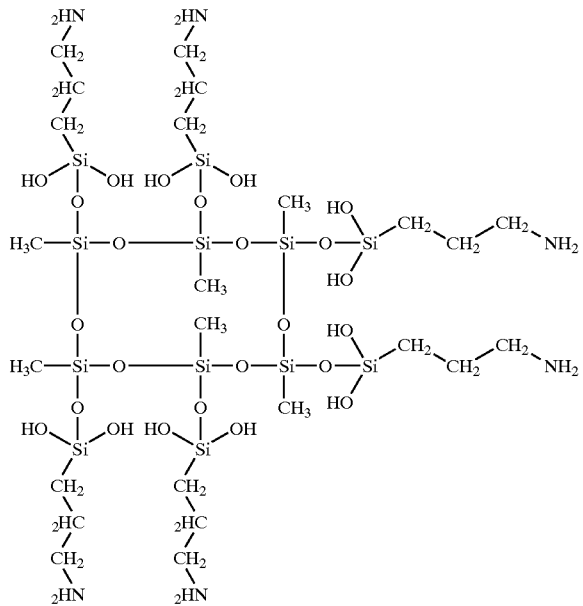

The silane oligomer hydrate of the formula (3) corresponds to the silane oligomer produced by copolymerizing aminopropyltrimethoxysilane as the aminosilane compound of the above formula (1) and a cyclic siloxane compound wherein $R^3$ is methyl, $R^4$ is methoxy, and n is 6, in the above formula (2).

The silane oligomer hydrate maintains a stable reaction equivalent rate so as to not participate in a further reaction since the terminal amino group is bonded to the terminal hydroxyl group via a hydrogen bond in the coating composition as shown in formula (3).

The silane oligomer hydrate is preferably present in an amount of 1 to 90 wt % in the total solution.

The present invention further provides a coating composition for preparing an immobilization layer for immobilizing a physiological material comprising a silane oligomer that is prepared by copolymerizing an aminosilane compound with a cyclic siloxane oligomeric compound. The hydrophilicity, the efficiency, the amount, and the shape of the immobilization layer can be controlled by using the silane oligomer hydrate comprising the cyclic siloxane oligomeric compound. The coating composition is environmentally friendly since both the silane oligomer hydrate and the dilution solvent are environmentally friendly.

The coating composition for preparing an immobilization layer may further comprise a dilution solvent. The dilution solvent is an organic solvent or a mixture of water and an organic solvent. The organic solvent is preferably an alcohol solvent such as methanol, ethanol, propanol, or butanol; a cellosolve solvent such as methyl cellosolve; any organic solvent compatible with water such as an acetone; dimethylfornamide; or any mixture thereof. The organic solvent is preferably present in an amount of 50 to 99.9 wt %.

The coating composition comprises the silane oligomer hydrate in an amount from 0.1 to 50 wt %. When the amount of the silane oligomer hydrate is less than 0.1 wt %, the immobilization layer for immobilizing the physiological material is not sufficiently formed, whereas when it is more than 50 wt %, the coating composition cannot be applied to the substrate, and the obtained coating layer is too thick to prevent cracking.

The substrate for immobilizing the physiological material comprises the immobilization layer that is prepared by the process comprising coating the composition comprising the silane oligomer on the substrate, and heat-treating the coated substrate to prepare the three-dimensional cross-linking structural immobilization layer through condensation of the silane oligomer.

The substrate may include a silicone wafer, glass, or a polymeric film such as polycarbonate, polystyrene, or polyurethane. The coating process of the composition may include any wet coating method such as dipping, spraying, spin-coating, or printing, but it is not limited thereto. The wet coating process is simpler and takes less time for forming the immobilization layer than the photolithography process disclosed in U.S. Pat. No. 5,985,551.

The silane oligomer coated on the substrate is condensed by thermosetting during the heat-treatment to provide an immobilization layer having a three dimensional cross-linking structure. The heat-treatment is preferably carried out at a temperature of 100 to 300° C. When the temperature is less than 100° C., the condensation is not sufficient, whereas when the temperature is more than 300° C. the amino group rapidly degenerates.

As shown in FIG. 1, the conventional immobilization layer 2 formed on the substrate 1 is a self-assembly-monolayer. The self-assembly-monolayer is manufactured for an extended duration, and it is difficult to obtain a functional group with a uniform density.

Figure 2:
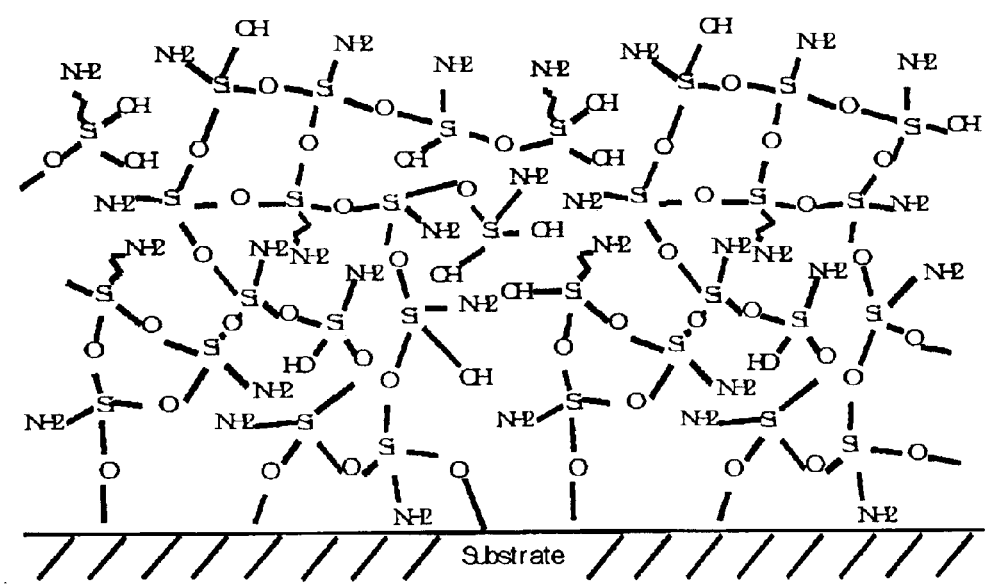
FIG. 2 is a cross-sectional view showing a substrate for immobilizing a physiological material having a three-dimensional cross-linking structure according to the present invention.

The present invention can provide the immobilization layer 20 with a three-dimensional cross-linking structure on the substrate 10 as shown in FIG. 2, so as to provide the functional group uniformly. Further, an immobilization layer with a high-density functional group is fabricated in a relatively short time.

The three dimensional cross-linking structure prevents elimination of the immobilization layer and detachment of the physiological material when being washed with solvents used during the immobilization or washing step. Therefore, the thermal stability and reagent resistance are improved due to the structural characteristics.

The density of the immobilization groups is determined by analyzing light emitted from fluorescence dye in the immobilization layer upon continuous irradiation of a laser beam, the dye being fluorescein isothiocyanate (FITC), tetraethylrhodamine isothiocyanate (SCN-TMR), or tetramethylrhodamine succinirnide (SIE-TMR), which are activated with isothiocyanate or succinimide ether.

The results of the density analysis indicate that the substrate for immobilizing a physiological material according to the present invention has a very stable immobilization functional group at a uniform and high density.

The present invention also provides a biochip fabricated by attaching the physiological material or the physiological material activated to have a functional group to the immobilization functional group on the substrate, and washing out the unreacted physiological material to form a predetermined physiological material pattern. The physiological material is preferably reacted with the immobilization layer for 1 to 24 hours.

The biochip is prepared by a process comprising: coating the composition comprising the silane oligomer on the substrate; heat-treating the coated substrate to prepare the three-dimensional cross-linking structural immobilization layer through condensation of the silane oligomer; immobilizing a physiological material by reacting the physiological material with the immobilization group; and patterning the physiological material by washing out unreacted physiological material.

The method for patterning the physiological material on the immobilization layer may be any method such as photolithography, piezoelectric printing, micropipeting, spotting, and the like.

According to the one example of the present invention, a method is provided for preparing a DNA chip that comprises immobilizing oligohexanes on the immobilization layer of the substrate and repeating this process. The DNA chip is reacted with the sample solution labeled with fluorescence dye under the hybridization condition for 1 to 24 hours, and detected light emitted from fluorescence upon continuous irradiation of a laser beam is signalized.

Hereinafter, the present invention will be explained in detail with reference to examples. These examples, however, should not in any sense be interpreted as limiting the scope of the present invention.

EXAMPLE 1

1.5 g of a methylsiloxane oligomer (n is 10 in the formula (2), trade name: XS31-B1410, manufactured by GE Toshiba Silicon Co.), and 3.55 g of 3-aminopropyltrimethoxysilane were mixed in a mixed solvent including 6 g of ethanol and 6 g of water. The pH of the solution was adjusted to pH 9.0 by adding acetic acid, and it was reacted at 60° C. for 8 hours to obtain a silane oligomer hydrate. 10 g of the silane oligomer hydrate and 90 g of ethanol were mixed to obtain a coating composition for forming an immobilization layer. A glass slide was dipped into and coated with the coating composition and dried at 120° C. for 60 minutes to form an immobilization layer on the glass slide.

EXAMPLE 2

1.0 g of methylsiloxane oligomer (n is 10 in the formula (2), trade name: XS31-B1410, manufactured by GE Toshiba Silicon Co.), and 4.0 g of 3-aminopropyltrimethoxysilane were mixed in a mixed solvent including 6 g of ethanol and 6 g of water. The pH of the solution was adjusted to pH 9.0 by adding acetic acid, and it was reacted at 60° C. for 8 hours to obtain a silane oligomer hydrate. 10 g of the silane oligomer hydrate and 90 g of ethanol were mixed to obtain a coating composition for forming an immobilization layer. A glass slide was dipped into and coated with the coating composition and dried at 120° C. for 60 minutes to form an immobilization layer on the glass slide.

EXAMPLE 3

1.5 g of methylsiloxane oligomer (n is 10 in the formula (2), trade name: XS31-B1420, manufactured by GE Toshiba Silicon Co.), and 3.55 g of 3-aminopropyltrimethoxysilane were mixed in a mixed solvent including 6 g of ethanol and 6 g of water. The pH of the solution was adjusted to pH 7.0 by adding acetic acid, and it was reacted at 60° C. for 8 hours to obtain a silane oligomer hydrate. 10 g of the silane oligomer hydrate and 90 g of ethanol were mixed to obtain a coating composition for forming an immobilization layer. A glass slide was dipped into and coated with the coating composition and dried at 120° C. for 60 minutes to form an immobilization layer on the glass slide.

COMPARATIVE EXAMPLE 1

1.5 g of methyltrimethoxysilane and 3.55 g of 3-aminopropyltrimethoxysilane were mixed in a mixed solvent including 6 g of ethanol and 6 g of water. The pH of the solution was adjusted to pH 7.0 by adding acetic acid, and it was reacted at 60° C. for 8 hours to obtain a silane oligomer hydrate. 10 g of the silane oligomer hydrate and 90 g of ethanol were mixed to obtain a coating composition for forming an immobilization layer. A glass slide was dipped into and coated with the coating composition and dried at 120° C. for 60 minutes to form an immobilization layer on the glass slide.

COMPARATIVE EXAMPLE 2

0.1 g of aminopropyltrimethoxysilane was added to 9.9 g of toluene to obtain a coating composition for forming an immobilization layer. A glass slide was dipped into the coating composition and coated therewith, followed by being dried at 120° C. for 60 minutes, consequently forming an immobilization layer on the glass slide.

COMPARATIVE EXAMPLE 3

The patterned substrate for immobilizing a physiological material of this Comparative Example is prepared according to the same process as in U.S. Pat. No. 5,985,551. First, a glass slide was dipped into a mixed solution including 50 g of 3-aminopropyltrimethoxysilane and 15 g of toluene for 20 minutes, and then agitated in toluene for 30 minutes to remove excess aminopropyltrimethoxysilane followed by washing twice and drying at 100° C. for 60 minutes to prepare a hydrophilic substrate with amino group. Subsequently, a blocking surface was formed by reacting the amino group with 4-nitrobenzyl chlorofornate as a temporary photolabile blocking material and then exposing the photoblocked substrate surface to light through a mask to create unblocked areas on the substrate surface with the unblocked amino group. The exposed surface of the substrate was reacted with perfluoroacylchloride to form a stable hydrophobic alkyl siloxane matrix. Then, this remaining photoblocked substrate surface was exposed to create patterned regions of the unblocked amino group to produce a patterned substrate having the derivatized hydrophilic binding site regions.

The immobilization layers of the substrates for immobilizing a physiological material according to Examples 1 to 3 and Comparative Example 1 to 3 were labeled with a dimethylformamide solution of FITC. A laser beam was continuously irradiated onto the immobilization layer and the light emitted from the FITC on the layer was detected by a ScanArray 5000 (manufactured by Packard Biochip Technology. Table 1 shows the results thereof.

TABLE 1

| | Fluorescence Strength (a.u.) |
| --- | --- |
| Example 1 | 30100 |
| Example 2 | 23800 |
| Example 3 | 32300 |
| Comparative Example 1 | 12330 |
| Comparative Example 2 | 6083 |
| Comparative Example 3 | 8000 |

Generally, the higher the fluorescence strength, the more the immobilization group remains. As shown in Table 1, the fluorescence strengths of Examples 1 to 3 are remarkably superior to those of Comparative Examples 1 to 3. It can be seen that the substrate for immobilizing a physiological material of the present invention can preserve the immobilization functional group at a stable and high density. The result of Comparative Example 3 indicates that reactivity of the immobilization functional groups were reduced through reaction between the immobilization functional group and the photolabile blocking material and the removal of photolabile blocking material, and that the photolithography technique is unfavorable for manufacturing a high-density immobilization layer.

Figure 3A:
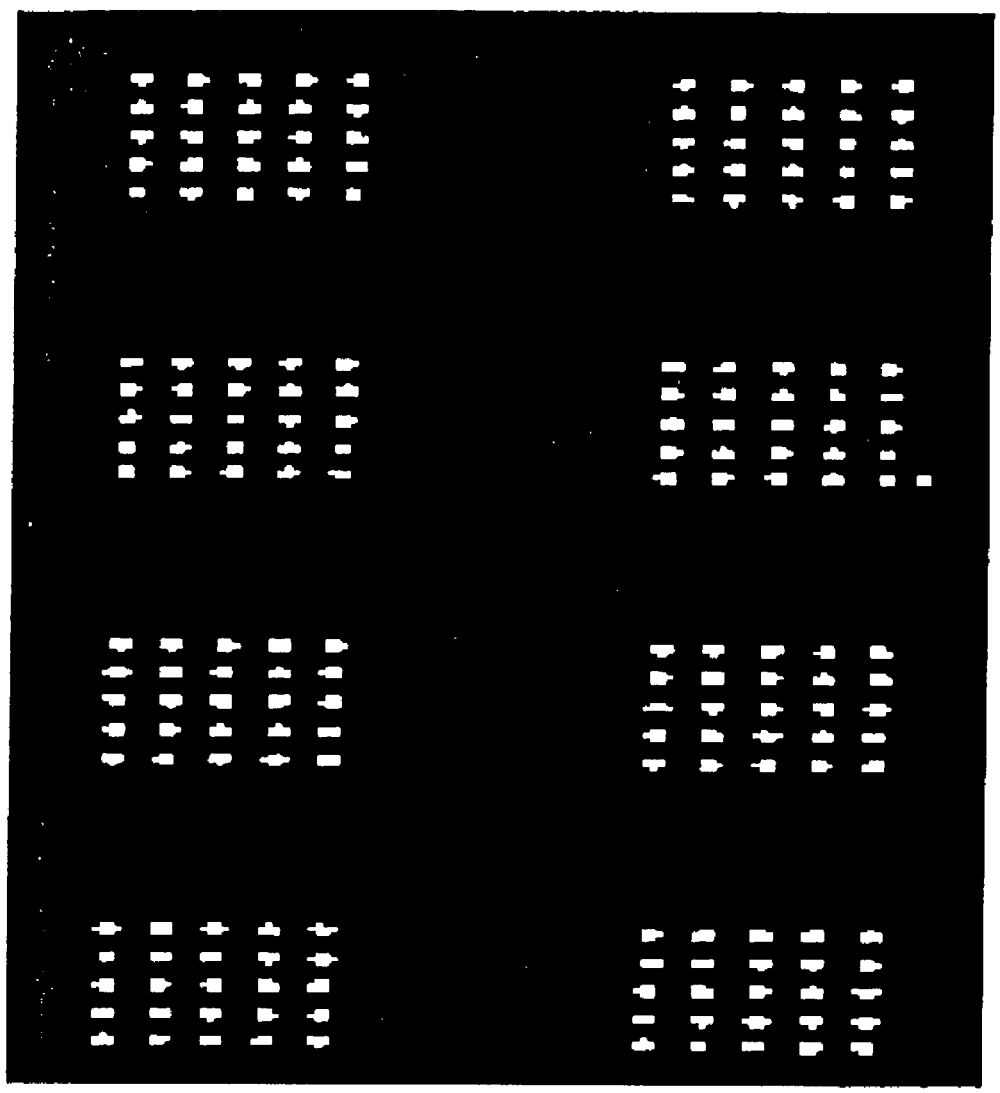
FIGS. 3A and 3B are photographs showing luminescence images of substrates for immobilizing a physiological material according to Example 3 and Comparative Example 1, respectively.
Figure 3B:
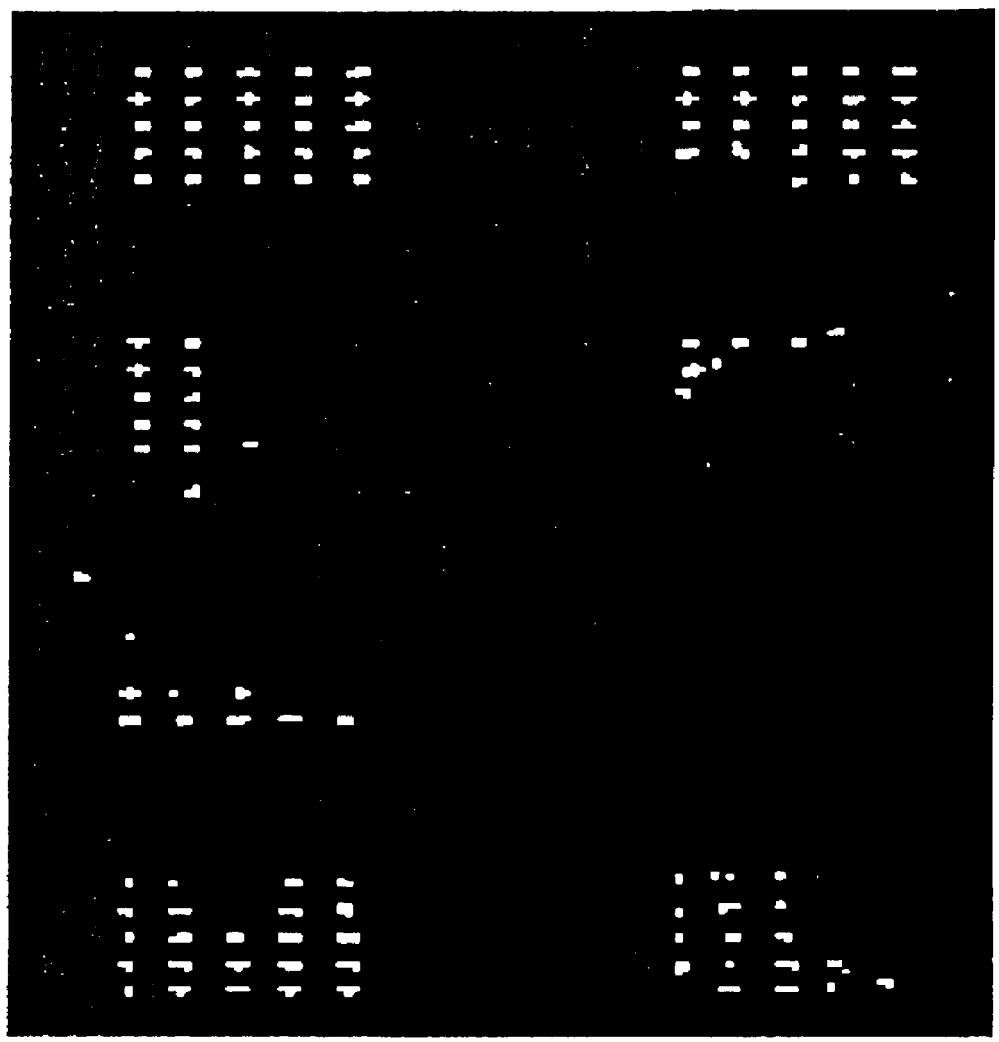

The substrates for immobilizing a physiological material according to Example 3 and Comparative Example 1 were immersed in boiling water at 100° C. for one hour and reacted with a probe DNA of oligonucleotides having 15 bases, so as to immobilize the DNA on the surface. Subsequently, the substrates were immersed in a sample solution containing a target DNA labeled with fluorescence dye Cy3 (available from Amersham Pharmacia, Inc.) and reacted with the target DNA, then washed to obtain a DNA chip. The DNA chip was irradiated with a laser beam, and the light emitted from the DNA chip was detected by a ScanArray 5000 (manufactured by Packard Biochip Technology). FIGS. 3A and 3B show the luminescence images of Example 3 and Comparative Example 3, respectively.

As shown in FIGS. 3A and 3B, the pattern of the DNA chip according to Example 3 is more definite and its luminescence strength is higher than that of Comparative Example 1. These results indicate that the immobilization group of Example 3 has superior thermal stability and reagent resistance than that of Comparative Example 1.

The present invention can preserve the immobilization layer by applying a silane oligomer. Further, the immobilization layer has a three-dimensional structure and thus has superior thermal stability and reagent resistance. The present invention can also provide a substrate for immobilizing a physiological material having an immobilization functional group with a uniform and high density by means of a simple process.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A silane oligomer for immobilizing a physiological material that is prepared by copolymerizing an aminosilane compound represented by the following formula (1) with a cyclic siloxane oligomeric compound represented by the following formula (2):

 (1)

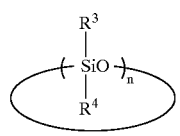 (2)

wherein
$R^1$ is selected from the group consisting of hydroxy and $C_{1-14}$ alkoxy;
$R^2$ is selected from the group consisting of $C_{1-14}$ alkyl groups, $C_{6-20}$ aromatic groups, ether groups, ester groups, and imine groups;
$R^3$ is $C_{1-12}$ alkyl;
$R^4$ is selected from the group consisting of hydroxy, $C_{1-14}$ alkoxy, halogen, and combinations thereof; and
n is an integer ranging from 5 to 30.

2. The silane oligomer according to claim 1, wherein the aminosilane compound of formula (1) and the cyclic siloxane oligomeric compound of formula (2) are provided in a mixed ratio of 0.01:99.99 to 90:10.

3. The silane oligomer according to claim 1, wherein the aminosilane compound of formula (1) is selected from the group consisting of 3-aminopropyltrimethoxysilane, 3-aminopropyltriethoxysilane, 2-aminoundecyltrimethoxysilane, aminophenyltrimethoxysilane, N-(2-aminoethylaminopropyl)trimethoxysilane, and combinations thereof.

4. The silane oligomer according to claim 1, wherein the compound of formula (2) is a cyclic methylsiloxane oligomeric compound.

5. A method for preparing an oligomer, comprising:
mixing an aminosilane compound represented by the following formula (1) with a cyclic siloxane oligomeric compound represented by the following formula (2)

 (1)

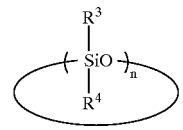 (2)

wherein
$R^1$ is selected from the group consisting of hydroxy and $C_{1-14}$ alkoxy,
$R^2$ is selected from the group consisting of $C_{1-14}$ alkyl groups, $C_{6-20}$ aromatic groups, ether groups, ester groups, and imine groups,
$R^3$ is $C_{1-12}$ alkyl,
$R^4$ is selected from the group consisting of hydroxy, $C_{1-14}$ alkoxy, halogen, and combinations thereof, and
n is an integer ranging from 5 to 30;
adding water to the mixture to prepare an aqueous solution; and
copolymerizing the aminosilane compound of formula (1) with the cyclic siloxane oligomeric compound of formula (2) while agitating the aqueous solution to obtain the silane oligomer in hydrate.

6. The method for preparing an oligomer according to claim 5, wherein the method further comprises adjusting the pH of the aqueous solution from 4 to 10 before the copolymerization reaction.

* * * * *